(12) United States Patent
Hirsch

(10) Patent No.: US 7,820,208 B2
(45) Date of Patent: Oct. 26, 2010

(54) METHOD OF ASSAYING SATIETY ENHANCING TASTANTS

(76) Inventor: Alan R. Hirsch, 7 Vernon Trail, Riverwoods, IL (US) 60015

( * ) Notice: Subject to any disclaimer, the term of this patent is extended or adjusted under 35 U.S.C. 154(b) by 0 days.

(21) Appl. No.: 12/355,494

(22) Filed: Jan. 16, 2009

(65) Prior Publication Data

US 2009/0123380 A1    May 14, 2009

Related U.S. Application Data

(62) Division of application No. 10/306,198, filed on Nov. 27, 2002.

(60) Provisional application No. 60/334,401, filed on Nov. 30, 2001.

(51) Int. Cl.
*A01N 65/00* (2009.01)
*A61K 49/00* (2006.01)

(52) U.S. Cl. .......... 424/725; 424/9.2; 514/909
(58) Field of Classification Search ............. None
See application file for complete search history.

(56) References Cited

U.S. PATENT DOCUMENTS 5,603,971 A * 2/1997 Porzio et al.

FOREIGN PATENT DOCUMENTS

EP          267735 A2 *  5/1988

* cited by examiner

*Primary Examiner*—Michele Flood
(74) *Attorney, Agent, or Firm*—Bryan Cave LLP

(57) ABSTRACT

Compositions for enhancing satiety and weight loss in an individual, assays for assessing a tastant for enhancing satiety and weight loss, and methods of using the composition to suppress appetite and enhance weight loss are provided.

20 Claims, No Drawings

METHOD OF ASSAYING SATIETY ENHANCING TASTANTS

CROSS-REFERENCE TO RELATED APPLICATIONS

This application is a divisional of U.S. patent application Ser. No. 10/306,198, filed Aug. 7, 2003, which claims the benefit of U.S. Provisional Application Ser. No. 60/334,401, filed Nov. 30, 2001.

FIELD OF THE INVENTION

The present invention relates generally to appetite suppression and weight loss, and more particularly to a composition that enhances satiety during a meal and methods of using the composition to achieve body weight loss.

BACKGROUND OF THE INVENTION

With a third to a quarter of the American population overweight, obesity is rampant in contemporary society. At any given time, 40% of women and 24% of men are trying to lose weight and of these, 84% of women and 76-78% of men are dieting for this purpose. In the USA, losing weight has become a national obsession. Over 30 billion dollars are spent each year devising a plethora of new diets and methods for losing weight, none of which have been demonstrated to be effective over a long term (2 years).

Obesity is one of the most pervasive health problems in our society. The physical and psychological consequences have an impact on the afflicted in countless ways.

Almost all overweight people suffer derision and ridicule, but the worst prejudice is reserved for and directed towards obese women. We need only look at television commentators, politicians, and other public life to realize that overweight men do not experience the same degree of discrimination that obese women suffer.

States of hunger and satiety are known to be of crucial importance in the regulation of weight, and the perception of hunger is multivariate; environmental stimuli, psychological substrate, and internal physiology all contribute a share. Everyday experiences attest to the influence of ambient aromas on our appetites; we salivate at the smell of freshly baked cookies and feel nauseated at a whiff of sewer gas. When we are hungry, foods smell better and therefore, taste better. Conversely, olfactory ability wanes when we are satiated, lessening the hedonics of further ingestion.

Anatomic connections of the olfactory bulb to the ventromedial nucleus of the hypothalamus, the satiety center, authenticate these observations, as does the presence of cholecystokinin, a gastic satiety factor, as a neurotransmitter in the olfactory bulb. The fact that patients with acute anosmia often gain weight suggests that a failure of the olfactory-satiety feedback mechanism may be involved.

In a study to assess the effect on inhalation of certain aromas upon weight control, overweight subjects were given an inhaler containing a blend of odorants and instructed to inhale three times in each nostril whenever feeling hungry. New inhalers containing a new blend of odorants were supplied each month over a period of six months. Data indicated that those subjects with normal olfactory abilities and who inhaled certain odorants, used their inhalers frequently, ate two to four meals a day, felt bad about overeating but not about themselves, lost nearly five pounds or two percent of body weight per month over the six-month period.

This procedure has several drawbacks including the need and inconvenience of using an inhaler prior to a meal to inhale the odorants, the conspicuous nature of the inhaler, and the need to carry the inhaler around.

Therefore, it would be desirable to provide a more effective and convenient appetite suppression technique.

SUMMARY OF THE INVENTION

The present invention relates to a composition for enhancing satiety, assays for assessing a tastant for enhancing satiety, and methods of using the composition to suppress appetite.

The invention is based, in part, on the discovery of a specific role for tastant substances in appetite suppression and body weight loss.

In one aspect, the invention provides a satiety enhancing composition. The composition comprises a tastant, which when applied to or admixed with food, is effective to enhance satiety (i.e., feeling of fullness), resulting in reduced food (caloric) intake during the meal. The satiety enhancing composition is preferably a dry, free-flowing powder form that can be sprinkled onto a foodstuff to be consumed. In one embodiment, the satiety enhancing composition comprises a primarily sweet tastant. In another embodiment, the composition comprises a primarily salty tastant. The tastant type is preferably used in conjunction with foodstuffs most appropriate to that taste type.

In another embodiment, the satiety enhancing composition comprises an amount of at least one tastant in combination with a carrier, and optionally with an anti-caking agent, a coloring agent, or both, which amount is effective to effect an average weight loss of about 0.5 lb. or more per month over an about 6-month period, when the composition is applied to and ingested with a foodstuff on a daily basis over the about 6-month period.

In another aspect, the invention may provide a method of enhancing satiety and suppressing appetite. In one embodiment, the method comprises applying a satiety enhancing composition to a foodstuff, the composition comprising an amount of a tastant which, when applied to a foodstuff and ingested, is effective to reduce caloric intake during a meal; and administering the food to a person for ingestion. In another embodiment, the method comprises selecting a satiety enhancing composition comprising a tastant; applying the satiety enhancing composition to a foodstuff; and administering the foodstuff to an individual for ingestion. In yet another embodiment, a method for controlling appetite in an individual includes selecting a tastant based on a foodstuff to be ingested and effectiveness of the tastant to enhance satiety; preparing a satiety enhancing composition comprising an amount of the tastant effective to reduce appetite when applied to and ingested with a foodstuff; applying an effective amount of the satiety enhancing composition to the foodstuff; and administering the foodstuff to a subject for ingestion, wherein the intake of food by the subject is reduced.

In another embodiment, a method for promoting weight loss in a person involves applying a satiety enhancing composition to a food to be ingested, the amount of tastant in the composition effective to cause a reduction in the intake of food by the person; and administering the food to the person for ingestion. The effect of the satiety enhancing composition can be measured, for example, by a reduction in body weight over a set time period, for example a 1-month period. Preferably, the application of the satiety enhancing composition to foodstuffs on a daily basis will effect a body weight loss of at least about 0.5 pound (lb.) per month, preferably at least about 1 lb. per month, preferably at least about 3 lbs. per month, to up to about 5 lbs. per month, preferably up to about 10 lbs. per month, preferably up to about 15 lbs. per month, and preferably about 5 lbs. to up to about 20 lbs. over an initial 6-month period, preferably up to about 25 lbs., preferably up to about 35 lbs.

In yet another embodiment, a method of promoting weight loss according to the invention involves combining an effective amount of a satiety enhancing composition with substantially each food portion to be consumed, on a daily basis over a one-month period, the composition comprising either a primarily sweet tastant or a primarily salty tastant as appropriate to the food type, and preferably, the same two tastant compositions being used over the month period, to effect a monthly weight loss of at least about 0.5 lb. to up to about 15 lbs. and, optionally, continuing such application of a satiety enhancing composition to substantially each food portion to be consumed over consecutive one-month periods for up to 6-months or longer to effect an about 5 lb. to an about 35 lb. weight loss over an about 6-month period, wherein the two compositions (i.e., comprising a primarily salty tastant or primarily sweet tastant) utilized during a subsequent one-month period comprise different tastants than the two compositions utilized in the preceding one-month period.

In another aspect, the invention provides a foodstuff comprising a food combined with a satiety enhancing composition according to the invention. In one embodiment, the foodstuff comprises an admixture of a primarily sweet food, and an amount of a satiety enhancing composition comprising a primarily sweet tastant effective to enhance satiety and/or suppress appetite resulting in reduced food intake upon ingestion of the foodstuff. In another embodiment, the foodstuff comprises an admixture of a primarily salty food and an effective amount of a satiety enhancing composition comprising an effective amount of a primarily salty tastant.

In yet another aspect, the invention provides a method for assaying tastants for a satiety enhancing effect and appetite suppression, or weight loss enhancing effect, when applied to or admixed with a foodstuff and ingested. In one embodiment, the assay method comprises selecting a tastant; formulating a composition consisting essentially of the tastant, a carrier, and optionally an anti-caking agent, a coloring agent, or both; applying an amount of the composition to a foodstuff; administering the foodstuff to the individual for ingestion; and assessing the effectiveness of the composition to reduce caloric intake during meals as measured, for example, by a reduction in body weight.

In another embodiment, a method of assaying a tastant for effecting weight loss of an individual, comprises the steps of: selecting a tastant based on a food to be ingested, the tastant selected from the group consisting of a primarily salty tastant or a primarily sweet tastant; formulating a composition consisting essentially of the tastant, a carrier, and optionally an anti-caking agent, a coloring agent, or both; combining the composition with each food to be ingested by an individual to form a foodstuff; wherein a composition comprising a primarily salty tastant is combined with a primarily salty food, and a composition comprising a primarily sweet tastant is combined with a primarily sweet food; administering each of said foodstuffs to the individual for ingestion; repeating the combining and administering steps on a daily basis for an at least one month period; and assessing the effectiveness of the composition to effect weight loss according to a change in weight of the individual. A preferred tastant is one that effects an average weight loss of about 0.5 lb. or more per month over an about 6-month period.

In another aspect, the invention provides an article of manufacture. In one embodiment, the article of manufacture comprises a unit amount of the satiety enhancing composition according to the invention contained within a packaging material, optionally with instructions for the use of the composition to enhance weight loss, or enhance satiety or suppress appetite for a resultant body weight loss, for example.

DETAIL DESCRIPTION OF THE INVENTION

In the current application, the term "tastant" is generally understood to include substances having a flavor quality (i.e., salty, sweet, sour, bitter) combined with an aromatic quality. All percentages are by weight based on the total composition, unless otherwise indicated.

The satiety enhancing composition of the invention can be formulated with one or more "sweet" tastants that impart a sweet taste, or one or more "salty" tastants that impart a salty or non-sweet taste. Examples of sweet tastants that can be used to achieve the benefits of the invention include almond (benzaldehyde), anise, carob, cinnamon, cocoa (natural cocoa nibs), malt, peanut (roasted), pecan, pistachio (natural), peppermint, spearmint, and fruit type tastants including apple (natural apple), banana, fig, kiwi, orange (sweet orange peel) peach, raisin, raspberry and strawberry, and the like, and mixtures or blends thereof. Examples of salty tastants that can be utilized according to the invention include artichoke, asparagus, avocado, basil, broccoli, celery seed, cucumber, fennel, garlic, horseradish, mushroom, mustard (seed), onion, parmesan, pizza, ranch, spinach, taco, white cheese (e.g., Romano), yellow cheese (e.g., cheddar), and the like, and mixtures or blends thereof.

The tastant can be a naturally-derived material or synthetically produced, according to methods known and used in the art. The tastant can be derived from concentrating the flavor components (extracts) of naturally occurring plants and herbs, and parts thereof. For example, the tastant can be extracted with a solvent (e.g., an alcohol/water mixture), and the extractant dried by spray drying or evaporation. The tastant can comprise a blend of natural or synthetic flavors.

Examples of formulations for the composition include crystalline, microcrystalline, particles, granules, powder, spray-dried, lyophilized, and the like, forms that will admix with a foodstuff to which it is applied, and dissolve or undergo disintegration or dissolution in the presence of fluids in the mouth, stomach and/or intestine. Preferably, the composition is in the form of a free-flowing powder or granules, and contains less than about 5 wt-% of moisture. The composition can also be in the form of an oil which is sprayed onto a carrier such as magnesium carbonate.

In a preferred form, the satiety enhancing composition is a powder or granular mixture of the tastant and a suitable finely divided solid (powder, granules) base or carrier, which is odorless and tasteless, compatible with other ingredients of the formulation, and not harmful to the recipient. Examples of such carriers include maltodextrin, dextrin, starch, methylcellulose, sodium carboxymethylcellulose, lactose, and the like, with maltodextrin being preferred.

The composition can further include an anti-caking agent such as tricalcium phosphate, and silicon dioxide (e.g., Flo-Gard AB silica), preferably in an amount of up to 2% by weight, based on the total weight of the composition. A compatible colorant and suitable for food (e.g., FD&C dyes) such as FD&C Yellow #5 (Alum Lake 24-28%) and carmine (Alum Lake based on carminic acid), can also be added, preferably in an amount of about 0.5% by weight or less, based on the total weight of the composition.

Other additives and adjuvants that can be included in the composition include effective but minor amounts of preservatives such as ascorbic acid and sodium ascorbate; and antimicrobial agents such as sodium benzoate, potassium benzoate, potassium sorbate, parabens, and the like.

The satiety enhancing composition can be prepared by dry mixing a solid form (e.g., powder or granules) of the tastant with a finely divided solid carrier, and optional ingredients as desired. The components of the composition can be admixed as is known in the art and formulated according to standard procedures. Preferably, each of the components of the composition is a FDA-GRAS approved food additive.

The satiety enhancing composition generally comprises the tastant in an amount of about 50% by weight up to about 99.98% by weight, based on the total weight of the composition. Typically, the tastant is included in an amount of about 50% to about 60% by weight, with the balance being a carrier and, optionally as desired, minor but effective amounts of an anti-caking agent and/or coloring agent. The amount of the tastant in the composition depends, at least in part, on the form of the tastant, and the strength of the desired taste, and the hedonic quality of the tastant. The composition generally comprises 0 to up to 0.5% by weight coloring agent, typically about 0.01% to about 0.03% by weight when included, and 0 to up to about 2% by of an anti-caking agent, typically about 0.5% to about 1% by weight when included, and about 40% to about 50% by weight carrier, based on the total weight of the composition. An exemplary satiety-enhancing composition comprises about 50% to about 60% by weight tastant (dry powder form), about 40% to about 50% by weight maltodextrin (granulated), 0 to about 1% by weight tricalcium phosphate, and 0 to about 0.03% by weight colorant, based on the total weight of the composition.

The satiety enhancing composition can be conveniently provided in discrete packaged amounts, for example, an amount to be used in a daily intake of food, or over a 1-month period of time. For example, the composition can be packaged as a powder form in hard or soft gelatin capsules, cartridges, blister packages, envelopes, tubes, vials, ampoules, bottles, lidded cylinders, a shaker-type container with holes for dispensing the composition, among other containers.

The amount of the tastant in a composition required for use in enhancing satiety may be varied or adjusted according to the particular application, the potency of the tastant selected, and the taste and olfactory threshold of the individual. An amount of the composition applied to each portion of food to be ingested in a day is effective in diminishing appetite and enhancing satiation, resulting in reduced calorie intake during the meal, as evidenced by body weight loss over a set time period. In general, a sufficient amount of the composition to provide the benefits of the invention for an average adult human is in an amount of about 1/16 tsp. to about 1 tsp. or more, typically about 1/16 tsp. up to about 1/2 tsp., per about 8 oz. of food (wet or dry weight), depending on the particular application. On average, an adult person consumes up to about 20 meals or snacks per day, and the composition is preferably applied to each food portion that is eaten on a daily basis. The upper amount of the composition that is added to the a food portion is generally limited by the taste preference and tolerance of the individual.

In use, a satiety enhancing composition comprising a tastant most appropriate to the taste type of the foodstuff (i.e., sweet or salty) is applied to (e.g., sprinkled onto), and optionally admixed with, the foodstuff, which is then consumed. Either a composition comprising a primarily salty tastant or tastant blend or a composition comprising a primarily sweet tastant or tastant blend can be used, depending on whether the foodstuff to be consumed is classified as a primarily "sweet" food or "salty" (non-sweet) food. The satiety enhancing composition is applied to or admixed with the foodstuff in an amount effective to extend the satiation effect of that foodstuff, and achieve appetite suppression and a reduction in caloric intake.

Examples of primarily "sweet" edible foodstuffs include sweet baked goods, cake, pudding, cookies, candy, pies, and the like. Examples of primarily "salty" edible foodstuffs include breads, baked goods, meats, poultry, seafood, stews, casseroles or baked dishes, potatoes, vegetables, cereal, potato chips, cheese curls, pretzels, crackers, and the like.

The satiety enhancing composition taken orally with a foodstuff results in the individual being satiated with a lower caloric intake. The satiety enhancing composition can be used with a weight loss program or diet to reduce appetite for food, and/or as a weight loss maintenance system. Preferably, the ingestion of the satiety enhancing composition with the foodstuff effectively suppresses food intake by about 10% to about 30%, which can be demonstrated by an associated body weight reduction over a set time period, for example, a 1-month period or more, over which a weight loss of about 0.5 lb. to up to about 5 lbs. or more per month can occur, preferably about 1 lb. to up to about 10 lbs. or more per month, preferably about 3 lbs. to about 15 lbs. per month, and up to about 20 lbs. over a 6-month period, preferably up to about 25 lbs., preferably up to about 35 lbs. over a 6-month period.

In a preferred use of the satiety enhancing composition to promote weight loss, a set of two satiety enhancing compositions are utilized continuously over a one-month period, the first comprising a primarily sweet tastant, and the second comprising a primary salty tastant, and applied to each food item that is consumed on a daily basis over the one-month period. Preferably, the procedure is continued over consecutive months, preferably up to at least about 6 months, utilizing a different set of two compositions containing a different sweet tastant or salty tastant than the preceding month. Preferably, such application of the compositions results in a body weight loss of at least about 0.5 lb. per month, preferably at least about 1 lb. per month, preferably at least about 3 lbs. per month, to up to about 5 lbs. per month, preferably up to about 10 lbs. per month, preferably up to about 15 lbs. per month, and about 5 lbs. to up to about 35 lbs. over an about 6-month period. The same set of compositions is preferably utilized over an entire month period. As such, a tastant not traditionally used on a particular foodstuff can be applied. For example, a peppermint tastant can be combined with a breakfast cereal, or a horseradish tastant with pizza, etc.

The satiety enhancing composition can be provided as an article of manufacture comprising a unit amount of the composition contained within the packaging material, wherein the composition comprises a tastant or blend of tastants in an amount effective to enhance satiety or suppress appetite. The packaging material is preferably a water impervious material. Exemplary packaging materials include a box, cylinder, cartridge, vial, ampoule, container with openings (covered) for dispensing the composition (i.e., a shaker), bottle, tube, blister package, envelope, hard or soft gelatin capsules, and the like. The packaging material includes instruction means that indicate that the satiety enhancing composition can be mixed with food and consumed to enhance satiety or suppress appetite. Suitable instruction means include printed labels, printed package inserts, tags, cassette tapes, CDs, computer discs, and the like.

Example 1

An open label study can be conducted as follows to assess the effect of individual tastants to induce body weight loss of an individual participant. An exemplary study group can include 15,000 adults based on the following criteria.

Inclusion/Exclusion Criteria

Inclusion criteria can be as follows:
1. Beyond ideal weight and not obese (body mass index (BMI) less than or equal to 30 kg m$^2$) (Mokdad et al., The continuing epidemics of obesity and diabetes in the United States, *JAMA* 286:1195-1200 (2001)).
2. Age 18-64
3. Likes to eat between meals
4. Does not exercise on a regular basis
5. Likes pickles or ice cream (separately)

Exclusion criteria can be as follows:
1. Pregnancy
2. Planning to become pregnant in the next 6 months.
3. Breast feeding
4. Perceived poor ability to taste
5. Uncontrolled hypertension, diabetes, or Sjorgren's syndrome The following satiety enhancing composition can be formulated with tastants in the amounts indicated.

TABLE 1

| Composition | Tastant | % by weight |
|---|---|---|
| Natural Apple Flavor Blend | natural apple flavor (Sensient)) | 60 |
| Roasted Peanut Flavor Blend | natural and artificial peanut butter flavor, powder (Gold Coast) | 60 |
| | natural peanut flavor (Sensient) | 2 |
| Raspberry Burst Flavor Blend | natural and artificial raspberry flavor (Gold Coast) | 50 |
| Blended Cinnamon Flavor | artificial cinnamon flavor, powder (Flavor Concepts) | 50 |
| Pistachio Flavor Blend | natural and artificial pistachio flavor (Sensient) | 60 |
| Cool Spearmint Flavor Blend | natural and artificial spearmint flavor (Gold Coast) | 50 |
| Rich Cocoa Flavor Blend | natural cocoa nibs flavor, powder (Carmi Flavor) | 50 |
| Banana Shake Flavor Blend | natural and artificial banana flavor (Gold Coast) | 50 |
| Horseradish Kick Flavor Blend | natural horseradish powder (SpiceTec-USF) | 70 |
| Supreme Garlic Flavor Blend | natural garlic flavor (Sensient) | 60 |
| Sharp Cheddar Cheese Flavor Blend | natural and artificial cheddar cheese flavor (Gold Coast) | 60 |
| Romano Cheese Flavor Blend | natural and artificial Romano cheese flavor (Gold Coast) | 60 |
| Yellow Onion Flavor | onion powder | 99.975 |
| Sharp Cheddar Cheese | natural and artificial cheddar cheese flavor (Gold Coast) | 50 |
| Sweet Apple Flavor | natural apple flavor powder WONF (Carmi Flavor) | 65 |

Methodology

A demographic questionnaire that documents, for example, age, race, sex, marital status, religion, employment status, alcohol consumption, smoking habits, drug usage, food preferences, eating habits, and so forth, can be completed by each participant.

Tastants and other ingredients of the tastant compositions are preferably FDA/GRAS approved. Compositions comprising an individual tastant or blends of tastants can be packaged in individual containers and labeled as either "salty" or "sweet", and coded such that the identity of tastant (or blend) in the composition is not revealed to the participant.

Each month, a participant can be given a one-month supply of two different satiety enhancing compositions, one containing a primarily sweet tastant (or blend thereof), and one containing a primary salty tastant (or blend thereof). The participant can be instructed to, each day, sprinkle an amount of the composition on all food, similar to how she/he would use salt or sugar, using a sweet tastant composition on primarily sweet foods, and a salty tastant composition on primarily salty foods. Participants can be told not to deviate from their usual diet and exercise habits. Two new test compositions can be provided each month for a period of 6 months. On initiation, subjects can complete written questionnaires regarding height and weight, hedonics (i.e., food preferences), demographics, and outlook (self-perception). The participants can be weighed monthly. Each month, two new tastant compositions can be provided, a questionnaire on weight, hedonics and outlook can be completed, and weight loss can be assessed as it relates to the tastants being tested and hedonics for the tastants.

The particular tastant composition, and frequency of the use of the compositions can be correlated with the amount of weight loss. Data can be analyzed, for example, using Pearson Correlation coefficients and I tests. Data can also be analyzed using Signed Rank Test, Wilcoxin Rank Sum Test, and Spearman's Rank Correlation Coefficient (T. Colton, *Statistics in Medicine*, Little Brown & Co., Boston, Mass. (1974); E. L. Lehmann, *Nonparametrics: Statistical Methods Based on Ranks*, Holden-Day, New York, N.Y. (1975)).

The expected results are a reduction in body weight and increase in self-esteem for the participant. In addition, the effectiveness of the different tastants that are tested can be assessed and rated.

Example 2

An open label study was conducted according to the protocol described in Example 1.

The Test Group included 92 adults: 73 females (79%) and 19 males (21%).

The Control group included 100 adults: 75 females (75%) and 25 males (25%).

Demographics. Each of the participants initially filled out a questionnaire regarding age, race, height, weight, amount of exercise per day and food preferences. The participants weighed themselves, and their body mass index was determined.

For the Test Group participants, the age range was 18 to 64 years old, with an average of 48 years of age. Race was reported as 74 Caucasians (80%), 14 African Americans (15%), 2 Hispanic (2%), and 2 "Other" (2%). The average amount of exercise per day was 15 minutes. The weight of the participants ranged from 130 to 348 pounds, with the average initial weight being 197 pounds. The body mass index (BMI) of the participants ranged from 25 to 49, with the average being a BMI of 31.

For the Control Group participants, the average initial weight was 192 lbs. and the average body mass index (BMI) was 30.

Protocol. Each of the Test Group participants were provided with two tastants compositions per month for a six month period, as shown below in Table 2.

The Test Group participants were instructed to sprinkle an amount of the tastant composition on all food each day, similar to how she/he would use salt or sugar, using a sweet tastant composition on primarily sweet foods, and a salty tastant composition on primarily salty foods. The participants weighed themselves monthly, and completed a questionnaire on hedonics of the tastant compositions.

The Control Group participants did not ingest tastant compositions with their food over the monitoring period.

TABLE 2

(Test Group)

| Month # | Salty Tastant | Sweet Tastant | Average Weight | Weight Change (lbs) | |
|---|---|---|---|---|---|
| | | | | Average Change | Range |
| Initial | — | — | 197 | — | — |
| 1 | Cheddar Cheese Flavor | Coca Flavor | 193.7 | −3.3 | −7 to +5 |
| 2 | Onion Flavor | Spearmint Flavor | 191.2 | −2.5 | −11 to +3 |
| 3 | Horseradish Flavor | Banana Flavor | 191.1 | −0.1 | −7 to +6 |
| 4 | Ranch Flavor | Strawberry Flavor | 190.8 | −0.3 | −5 to +12 |
| 5 | Taco Flavor | Raspberry Flavor | 191.4 | +0.6 | −6 to +9 |
| 6 | Parmesan Flavor | Malt Flavor | 191.4 | −0.0 | −1 to +1 |
| Final | | | 191.4 | −5.6 (−2.8%) | (−34 to +6) |

Results. The monthly average weight loss of the Test Group ranged from 0 lbs. (month 6) to −3.3 lbs. (month 1). The overall 6-month average weight change of the Test Group was a loss of −5.6 lbs., or an average weight loss of about −3%.

By comparison, the overall 6-month average weight change of the Control Group was a gain of +1.1 lbs., or an average weight gain of +0.6%.

This indicates an average overall improvement in the Test Group of −6.7 lbs. (from −5.6 lbs. to +1.1 lbs.).

The Test Group also had an average −2.8% change in body mass index (from an average BMI of 31 to 28.2), while the Control Group showed substantially no change.

Discussion. The results show that tastants (flavorants) may be used as a way of inducing weight loss in those attempting to lose weight, and can be integrated into a comprehensive weight loss program.

The invention has been described by reference to detailed examples and methodologies. These examples are not meant to limit the scope of the invention. It should be understood that variations and modifications may be made while remaining within the spirit and scope of the invention, and the invention is not to be construed as limited to the specific embodiments disclosed. The disclosures of references cited in the application are incorporated by reference herein

What is claimed is:

1. A method of assaying a set of tastants for effecting weight loss, the method comprising
    providing a group of individuals with a set of compositions consisting essentially of a tastant, a carrier, and optionally an anti-caking agent, a coloring agent, or both; one of the compositions in the set comprising a primarily salty tastant and another of the compositions in the set comprising a primarily sweet tastant;
    instructing the individuals to combine the compositions over a period of time with all food consumed during the period, the period being at least one month, the individuals being instructed to combine the composition comprising the primarily salty tastant with primarily salty foods and the composition comprising the primarily sweet tastant with primarily sweet foods; and
    after the period ends, determining whether the individuals of the group lost weight during the period of time.

2. The method of claim 1 wherein each of the compositions is in the form of a free-flowing powder or granules.

3. The method of claim 2 wherein each of the compositions comprises a carrier selected from the group consisting of maltodextrin, dextrin, starch, methylcellulose, sodium carboxymethylcellulose, and lactose.

4. The method of claim 1 wherein the primarily sweet tastant is selected from the group consisting of almond, anise, carob, cinnamon, cocoa, malt, peanut, pecan, pistachio, peppermint, spearmint, fruit tastants, and combinations thereof.

5. The method of claim 1 wherein the primarily salty tastant is selected from the group consisting of artichoke, asparagus, avocado, basil, broccoli, celery seed, cucumber, fennel, garlic, horseradish, mushroom, mustard, onion, parmesan, pizza, ranch, spinach, taco, white cheese, yellow cheese, and combinations thereof.

6. The method of claim 2 wherein the primarily sweet tastant is selected from the group consisting of almond, anise, carob, cinnamon, cocoa, malt, peanut, pecan, pistachio, peppermint, spearmint, fruit tastants, and combinations thereof.

7. The method of claim 2 wherein the primarily salty tastant is selected from the group consisting of artichoke, asparagus, avocado, basil, broccoli, celery seed, cucumber, fennel, garlic, horseradish, mushroom, mustard, onion, parmesan, pizza, ranch, spinach, taco, white cheese, yellow cheese, and combinations thereof.

8. The method of claim 1 wherein the period extends over consecutive months and the individuals are instructed to combine the compositions with all foods for the period of consecutive months wherein the primarily sweet tastant utilized in a subsequent month is different from the primarily sweet tastant utililized in the preceding month and the primarily salty tastant utilized in a subsequent month is different from the primarily salty tastant utilized in the preceding month.

9. The method of claim 8 wherein the individuals are instructed to apply the compositions onto foods for six consecutive months or longer.

10. The method of claim 8 wherein each of the compositions is in the form of free-flowing powder or granules.

11. The method of claim 9 wherein the each of the compositions is in the form of free-flowing powder or granules.

12. The method of claim 8 wherein the primarily sweet tastant is selected from the group consisting of almond, anise, carob, cinnamon, cocoa, malt, peanut, pecan, pistachio, peppermint, spearmint, fruit tastants, and combinations thereof.

13. The method of claim 8 wherein the primarily salty tastant is selected from the group consisting of artichoke, asparagus, avocado, basil, broccoli, celery seed, cucumber, fennel, garlic, horseradish, mushroom, mustard, onion, parmesan, pizza, ranch, spinach, taco, white cheese, yellow cheese, and combinations thereof.

14. The method of claim 9 wherein the primarily sweet tastant is selected from the group consisting of almond, anise, carob, cinnamon, cocoa, malt, peanut, pecan, pistachio, peppermint, spearmint, fruit tastants, and combinations thereof.

15. The method of claim 9 wherein the primarily salty tastant is selected from the group consisting of artichoke, asparagus, avocado, basil, broccoli, celery seed, cucumber, fennel, garlic, horseradish, mushroom, mustard, onion, parmesan, pizza, ranch, spinach, taco, white cheese, yellow cheese, and combinations thereof.

16. The method of claim 10 wherein the primarily sweet tastant is selected from the group consisting of almond, anise, carob, cinnamon, cocoa, malt, peanut, pecan, pistachio, peppermint, spearmint, fruit tastants, and combinations thereof.

17. The method of claim 10 wherein the primarily salty tastant is selected from the group consisting of artichoke, asparagus, avocado, basil, broccoli, celery seed, cucumber, fennel, garlic, horseradish, mushroom, mustard, onion, parmesan, pizza, ranch, spinach, taco, white cheese, yellow cheese, and combinations thereof.

18. The method of claim 11 wherein the primarily sweet tastant is selected from the group consisting of almond, anise, carob, cinnamon, cocoa, malt, peanut, pecan, pistachio, peppermint, spearmint, fruit tastants, and combinations thereof.

19. The method of claim 11 wherein the primarily salty tastant is selected from the group consisting of artichoke, asparagus, avocado, basil, broccoli, celery seed, cucumber, fennel, garlic, horseradish, mushroom, mustard, onion, parmesan, pizza, ranch, spinach, taco, white cheese, yellow cheese, and combinations thereof.

20. The method of claim 1 wherein the individuals are instructed to apply the compositions onto foods for six consecutive months or longer.

* * * * *